United States Patent [19]
Abdel-Rahman

[11] Patent Number: 6,163,031
[45] Date of Patent: Dec. 19, 2000

[54] IONIZATION DETECTOR SYSTEM HAVING LINEARIZED OUTPUT SIGNAL

[75] Inventor: Mahmoud F. Abdel-Rahman, West Grove, Pa.

[73] Assignee: Agilent Technologies, Inc., Santa Clara, Calif.

[21] Appl. No.: 09/070,005

[22] Filed: Apr. 30, 1998

[51] Int. Cl.[7] .................................................. G01T 1/18
[52] U.S. Cl. ........................................ 250/374; 250/252.1
[58] Field of Search ..................................... 250/374, 381, 250/379, 384, 252.1; 324/464, 455; 73/28.02

[56] References Cited

U.S. PATENT DOCUMENTS

| | | |
|---|---|---|
| 4,789,783 | 12/1988 | Cook . |
| 4,975,648 | 12/1990 | Lawson et al. . |
| 5,153,519 | 10/1992 | Wentworth et al. . |
| 5,317,271 | 5/1994 | Wentworth et al. . |
| 5,394,090 | 2/1995 | Wentworth et al. . |
| 5,394,091 | 2/1995 | Wentworth et al. . |
| 5,394,092 | 2/1995 | Wentworth et al. . |
| 5,528,150 | 6/1996 | Stearns et al. . |
| 5,532,599 | 7/1996 | Stearns et al. . |
| 5,541,519 | 7/1996 | Stearns et al. . |
| 5,594,346 | 1/1997 | Stearns et al. . |
| 5,804,828 | 9/1998 | Abdel-Rahman ................. 350/381 |

OTHER PUBLICATIONS

G. Gremaud, W. E. Wentworth, A. Zlatkis, R. Swatloski, E.C.M. Chen, S. Stearns, "Windowless Pulsed–Discharged Photoionization Detector Application To Qualitative Analysis Of Volatile Organic Compounds", accepted Aug. 18, 1995, Journal of Chromatography A. 724 (1996) pp. 235–250.

Herbert H. Hill and Dennis G. McMinn, Dept. of Chemistry, Washington State University, Pullman, Washington; "Detectors for Capillary Chromatography"; Chemical Analysis Series, vol. 121; ISBN 0–471 50645–1; 1992 John Wiley & Sons, Inc.

Primary Examiner—Seungsook Ham
Assistant Examiner—Richard Hanig

[57] ABSTRACT

Linearization of an ionization detector is obtained by processing the output signal derived from the ionization detector so as to compensate for the naturally-occurring logarithmic decay of the detector response at high sample concentrations. Linearization is accomplished according to a linearizing formula:

$$I_{(lin)} = I[1 + (I/I_{(dec)})]^{pwr}$$

where:

$I_{(lin)}$ = linearized output signal current of the detector $I$ = non-linearized output signal current of the detector $I_{(dec)}$ = output signal current at onset of logarithmic decay pwr = a power factor that compensates for the slope of the logarithmic decay

1 Claim, 5 Drawing Sheets

IONIZATION DETECTOR SYSTEM HAVING LINEARIZED OUTPUT SIGNAL

FIELD OF THE INVENTION

This invention relates generally to detectors for analysis of a sample gas; and more particularly, to an ionization detector system having a linearized output signal.

BACKGROUND OF THE INVENTION

Ionization detector sensitivity may be measured in a plot of detector response versus analyte concentration or analyte quantity. The range over which the detector sensitivity is constant is called the linear dynamic range, and the entire range over which response varies with concentration or quantity is called the dynamic range of the detector. The presence of a substantial concentration of analyte molecules in the detection zone of an ionization detector will consume a significant portion of the available concentration of ionizing particles. If the concentration of analyte molecules increases further, ionization of the analyte molecules can occur only at a decreasing rate and the detector response factor can be expected to decrease progressively. The upper limit of the dynamic range is determined when detector sensitivity falls to an unusable value, typically zero, and the detector is said to be saturated. The lower limit of the dynamic range occurs at a minimum detectable level (MDL).

Conventional ionization detectors suffer from nonlinearity due to the limited number of ionizing particles available for ionization, and as a result, the conventional ionization detector exhibits a linear dynamic range that is less than desirable. Particular examples of ionization detectors include the electron capture detector and the discharge ionization detector.

Electron capture detectors for gas chromatography are well known in the art. The electron capture detector (ECD) is extremely sensitive to certain molecules such as alkyl halides, but is relatively insensitive to hydrocarbons, alcohols, ketones, etc. This type of detector features high sensitivity and high selectivity towards electrophilic compounds and is widely used for detecting trace amounts of pesticides in biological systems and in food products. Such compounds typically contain halogens which combine with free electrons created in an ionization cell in the detector. The resulting decrease in free electrons in the ionization cell is monitored and used as an indication of the concentration of the compounds in a sample.

The response of the typical electron capture detector has been observed to be dependent upon many variables, such as the molecular composition of the sample and its concentration, the cleanliness and temperature of the detector cell, and the flow rates of the make-up gas and effluent. However, the behavior of the electron capture detector with regard many of these variables is not completely understood. For example, under apparently unvarying conditions, some constant current electron capture detectors can exhibit symptoms of a nonlinear and unpredictable relationship between the measured response and analyte concentration.

A discharge ionization detector operates by applying a high voltage across discharge electrodes that are located in a gas-filled chamber. In the presence of a noble gas such as helium, a characteristic discharge emission of photons occurs. The photons irradiate an ionization chamber receiving a sample gas that contains an analyte of interest. Ions are produced in the ionization chamber as a result of photon interaction with ionizable molecules in the sample gas. Helium metastables are also generated in the source chamber and are found to play a role in ionization of the analyte of interest.

FIG. 1 illustrates a detector response plot 200 recorded with use of a known helium discharge ionization detector. In the illustrated detector response plot, the analyte is carbon-12 ($C_{12}$). The normalized response factor should ideally be constant irrespective of the amount of the analyte introduced into the detector. As illustrated, the normalized response factor is flat in a linear dynamic range 210 but decreases in a second, non-linear region 220 when higher amounts of analyte are introduced to the detector.

Although the design of ionization detectors continues to be an object of study in the prior art, there nonetheless exists a need for an ionization detector having a detector response that exhibits an improved dynamic range.

SUMMARY OF THE INVENTION

The present invention is directed to a method and apparatus for providing a linearized output signal in an ionization detector, to thereby effect an improved dynamic range. The present invention will find advantageous use in all types of ionization detectors which suffer from a nonlinear dynamic range due to operation with a limited amount of ionizing particles.

Detector response in an ionization detector is based on an accurate measurement of the ionized analyte of interest. Linearization of the output signal of the detector will improve certain characteristics of the detector response, such as the linear dynamic range. Linearization of an ionization detector according to the present invention may be obtained by processing the output signal derived from the ionization detector so as to compensate for the decay of the response at high sample concentrations.

I have found by empirical determination that this decline in linearity is logarithmic and can be well compensated by altering the detector output signal current according to a linearizing formula:

$$I_{(lin)} = I[1 + (I/I_{(dec)})]^{pwr}$$

Where:

$I_{(lin)}$ = linearized output signal current of the detector $I$ = non-linearized output signal current of the detector $I_{(dec)}$ = output signal current at onset of logarithmic decay pwr = a power factor that compensates for the slope of the logarithmic decay In the above equation, little or no alteration is necessary to the output signal current in a range wherein the output signal current value is lower than $I_{(dec)}$. At output signal currents larger than $I_{(dec)}$, the non-linearized output signal must be increased to provide the linearized current $I_{(lin)}$.

The necessary values for $I_{(dec)}$ and pwr are empirically determined from a (computation of the response of log [$I$] versus log [analyte amount]. The values for $I_{(dec)}$ and pwr will be understood to be characteristic of a particular detector and are influenced by parameters pertinent to the particular construction of the ionization detector, such as the dimensions of the detector, or the power of the discharge source in a discharge ionization detector.

In a preferred embodiment of the invention, implementation of this linearizing formula can be accomplished via signal processing of the detector signal by way of a linearizing section interposed between the ionization detector output and the ancillary apparatus which may benefit from receiving a linearized output signal. The preferred linearizing section may thus may be implemented in discrete electronic circuitry (i.e., in hardware), in firmware operable in, e.g., an embedded processor or digital signal processor, or in software operable in a programmable computer.

Such linearization of the output response may be applied to any ionization detector operating according to the above-described limited concentration of ionizing particles. Ionization detectors that may benefit from the teachings of the present invention include, for example, a helium ionization detector, and argon ionization detector, an electron capture detector, a discharge ionization detector, and a photo ionization detector.

BRIEF DESCRIPTION OF THE DRAWINGS

The foregoing and other features and advantages of the invention will be apparent from the following more particular description of preferred embodiments of the drawings, in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

The apparatus and methods of the present invention may be employed in particular to improve the detection of an analyte that may be present in a variety of fluids. Gases are the preferred fluids according to the practice of the present invention, and therefore the following description of the invention will include a description of the arrangement, construction, and operation of a novel discharge ionization detector for use in a gas sample analytical system. The teachings of this invention apply to any detector operating on the principle of ionization of a fluid mixture, and as such include a discharge ionization detector, a helium ionization detector, an argon ionization detector, electron capture detector, and other detectors having either radioactive or non-radioactive electron sources.

Embodiments of the invention described herein are contemplated for use in an ionization detector, and in particular in a discharge ionization detector or in an electron capture detector, in a gas chromatograph. However, other applications such as process sampling systems, gas leak detection systems, air quality monitoring systems, and the like are contemplated.

In accordance with the present invention, a preferred linearizing formula may be implemented in a linearizing section having discrete electronic circuitry (i.e., hardware), or operable according to firmware or software.

Figure 1:
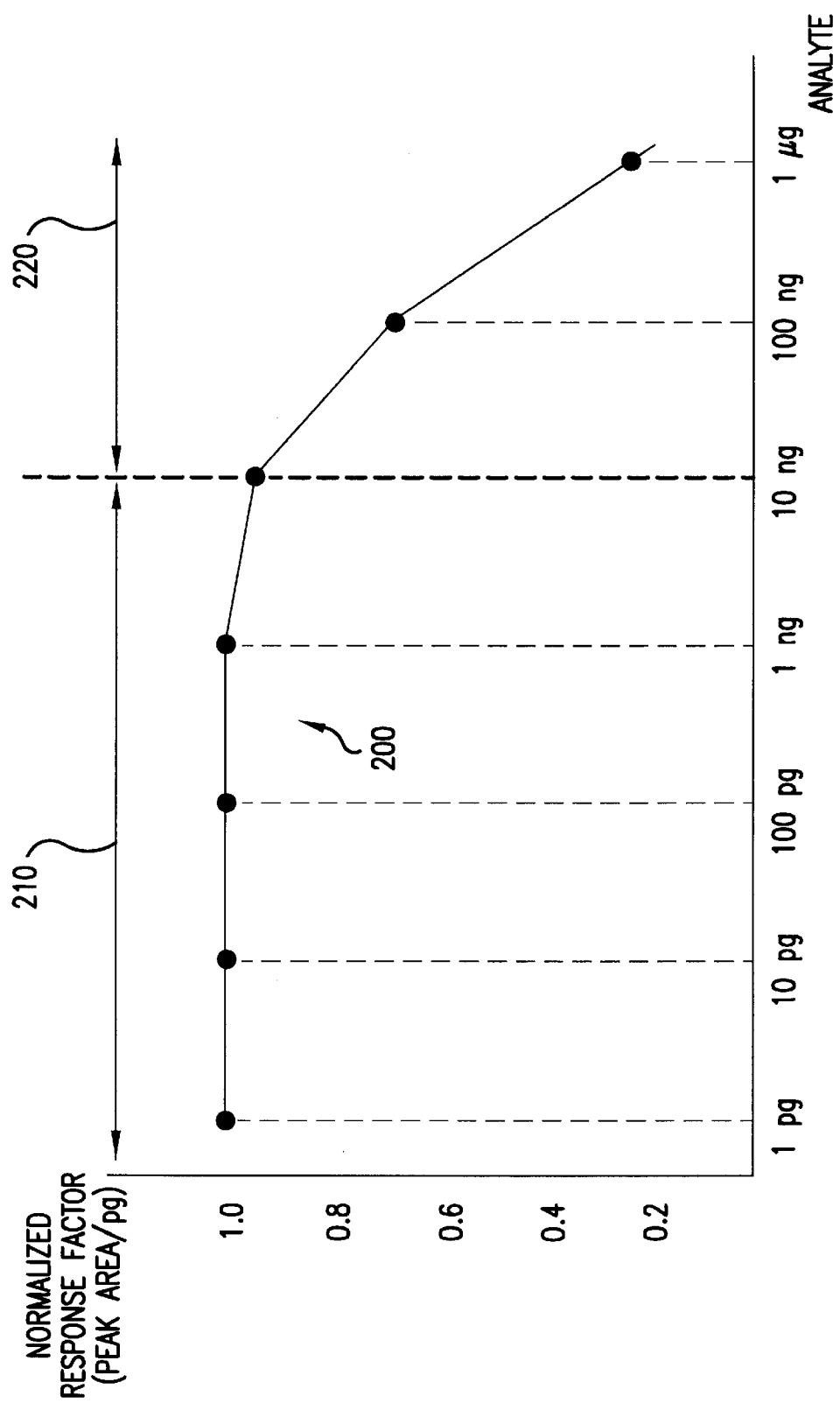
FIG. 1 is a graphical representation of the normalized response factor exhibited by a conventional ionization detector of the prior art.
Figure 2A:
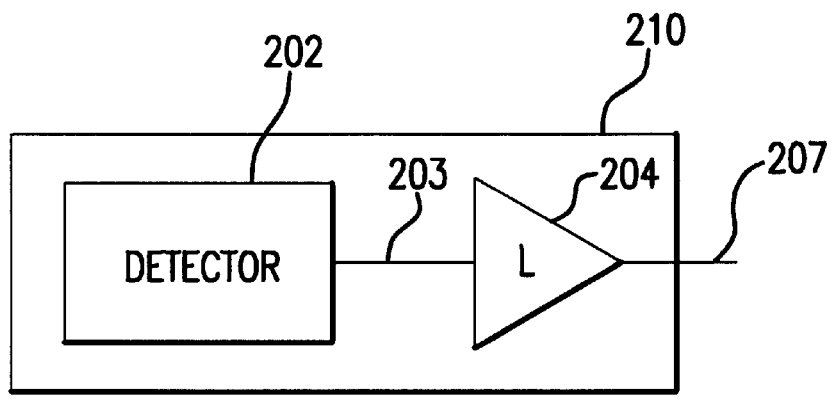
FIGS. 2A–2C are simplified schematic representations of preferred embodiments of a linearized ionization detector system constructed according to the present invention.
Figure 2B:
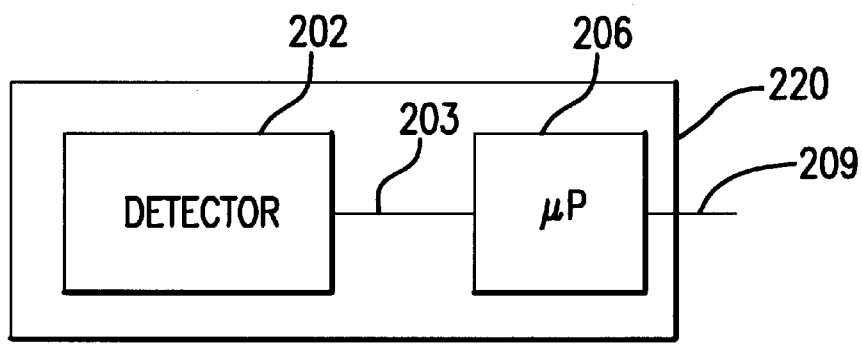
Figure 2C:
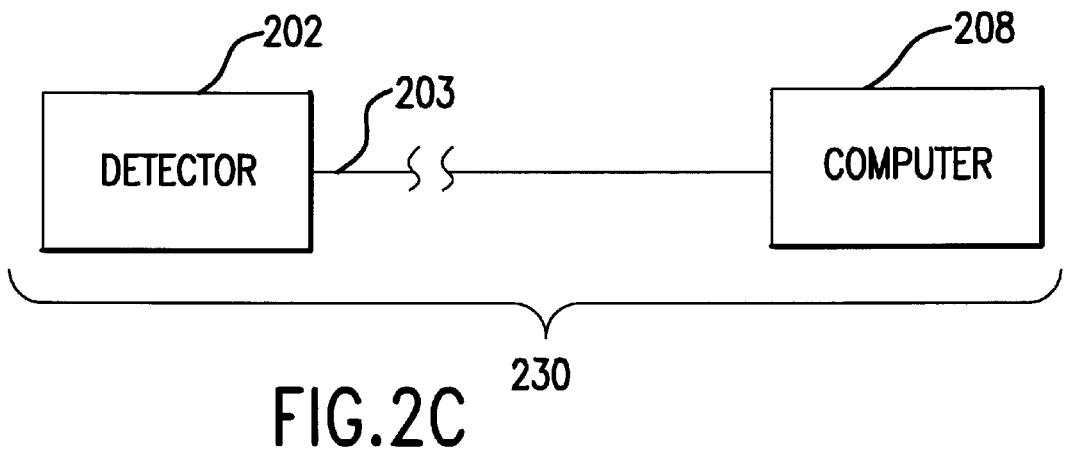

As illustrated in FIGS. 2A–2C, preferred embodiments of a linearized ionization detector system 210, 220, 230 are constructed to include an ionization detector 202 having non-linearized output signal supplied on an output signal line 203 that it is connected to a linearizing section in the form of an active linearizing circuit 204, or a linearizing signal processing unit 206, or a programmable computer 208 that includes a programming for carrying out the linearization described herein. The output signal of the detector 202 is compensated by altering the non-linearized output signal according to the linearizing formula:

$$I_{(lin)} = I[1 + (I/I_{(dec)})]^{pwr}$$

Where:
$I_{(lin)}$ = linearized output signal current of the detector
$I$ = non-linearized output signal current of the detector
$I_{(dec)}$ = output signal current at onset of logarithmic decay
pwr = a power factor that compensates for the slope of the logarithmic decay The above equation indicates that at a output signal current value lower than $I_{(dec)}$ the linearization is slight. At output signal currents larger than $I_{(dec)}$, the linearized current $I_{(lin)}$ becomes progressively greater than the non-linearized output signal current of the detector. The values for $I_{(dec)}$ and pwr are empirically determined and will be understood to vary according to the design parameters pertinent to the particular construction of the ionization detector, such as the dimensions of the detector, or the power of the discharge source in a discharge ionization detector.

Figure 3:
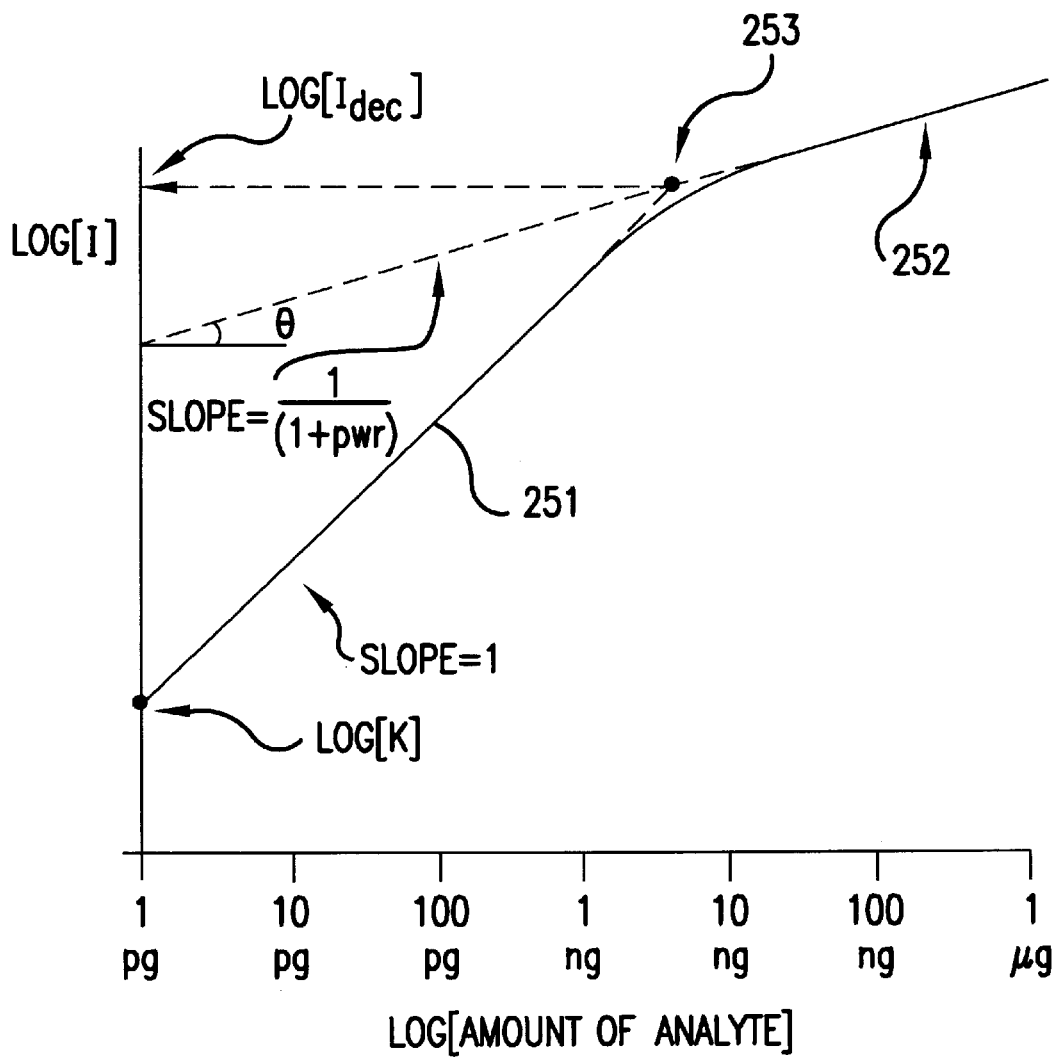
FIG. 3 is a graphical representation of a particular response factor plot calculated according to the present invention.

As illustrated in FIG. 3, the values for $I_{(dec)}$ and pwr are empirically determined from a plot of Log [I] versus Log [analyte amount]. In accordance with the relationship of $$I = k(A)$$

where
k = the linear response factor
A = analyte concentration the lower portion of the plot, the linear response plot 251, is observed to describe the linear response factor and exhibits a slope of 1; the upper portion of the plot, the non-linear response plot 252, is observed to describe the non-linear response and has a slope as follows:

$$\text{slope of non-linear response} = 1/[1+\text{pwr}]$$

and thus the angle Φ may be observed to define the value of pwr as follows:

$$\tan[\text{angle}\Phi] = 1/[1+\text{pwr}]$$

Accordingly, observation of the angle Φ allows one to compute the value of pwr. A value for $I_{(dec)}$ may be calculated from the value of Log [I] observed at the point 253 of the intersection of the linear response plot 251 and the non-linear response plot 252.

Figure 4:
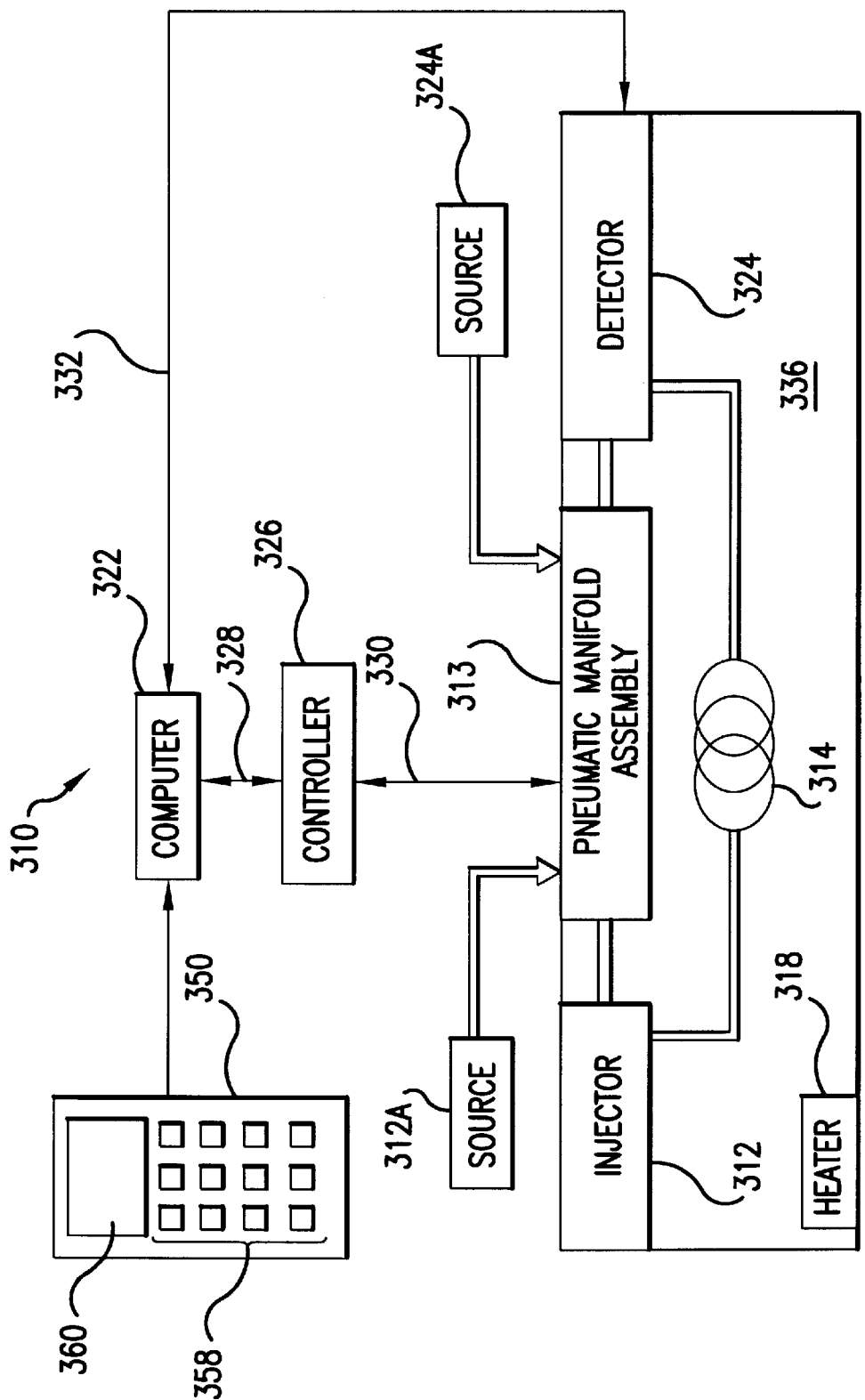
FIG. 4 is a simplified schematic representation of an analytical instrument having an ionization detector that offers a linearized detector response according to the present invention.

Accordingly, a novel ionization detector may be designed for use in an analytical instrument as shown in FIG. 4. The instrument is generally designated chromatograph 310. In the preferred embodiment, the chromatograph 310 is a Hewlett-Packard HP6890 gas chromatograph that is modified to include a novel ionization detector 324 constructed according to the teachings herein.

Operation of the chromatograph 310 may be generally understood as follows. In order to perform a chromatographic separation of a given sample compound, a sample is injected with a pressurized carrier gas by means of an injector 312. The carrier gas supplied to injector 312 is provided from a source 312A through one or more pneumatic manifold assemblies 313, each of which serves in part to control and redirect a plurality of gas flows, including the carrier gas and one or more detector gas of appropriate types. The detector gas are provided from respective sources (one such source 324A is shown) to the pneumatic manifold assembly 313. Suitable fluid-handling devices such as valves, sensors and the like in the pneumatic manifold assembly 313 are operated under the control of the computer 322 and controller 326 by way of control signals provided on a data and control lines 328, 330, 332. The control and data line 330 also allows the return of sense information from suitable sensors and signal-interface electronics that are provided in the pneumatic manifold assembly 313. Another set of data and control lines 332 allows the transfer of detector output signal information between the detector 324 and the computer 322.

A separation column 314 is positioned within an oven 336. The carrier gas/sample combination passing through column 314 is exposed to a temperature profile resulting in part from the operation of a heater 318 within oven 336. During this profile of changing temperatures, the sample will separate into its components primarily due to differences in the interaction of each component with the column 314 at a given temperature. As the components exit column 314 they are detected by the detector 324.

Computer 322 maintains overall control of the systems associated with chromatograph 310. It will be recognized that any particular gas chromatograph may include more systems than those described in relation to the present invention. For example, an electronic control panel 350 is shown to include an operator interface provided in the form of a keypad 358 and a display 360. It will also be understood that although computer 322 is shown as a single block, other embodiments are contemplated; for example, the functions of the computer 322 may be subsumed into one unit. The computer 322 includes a central processing unit and all associated peripheral devices, such as random access memories, read-only memories, input/output isolation devices, clocks, and, preferably, a digital signal processing unit, and other related electronic components. In the preferred embodiment, the central processor used in computer 322 is a microprocessor. As such, computer 322 may include a memory in which information and programming can be stored and retrieved by known methods. It will be appreciated that the programmed control of the computer 322 for effecting signal alteration in the linearization scheme described can be implemented by known programming techniques in accordance with the teachings herein. Alternatively, there may be provided a digital computing means, such as an digital signal processor (dsp) or embedded microprocessor, either of which may implement a linearization scheme as described herein via firmware, or a dedicated analog network circuit may incorporated in the output signal path from the detector 324 to implement the linearization scheme described herein.

Figure 5:
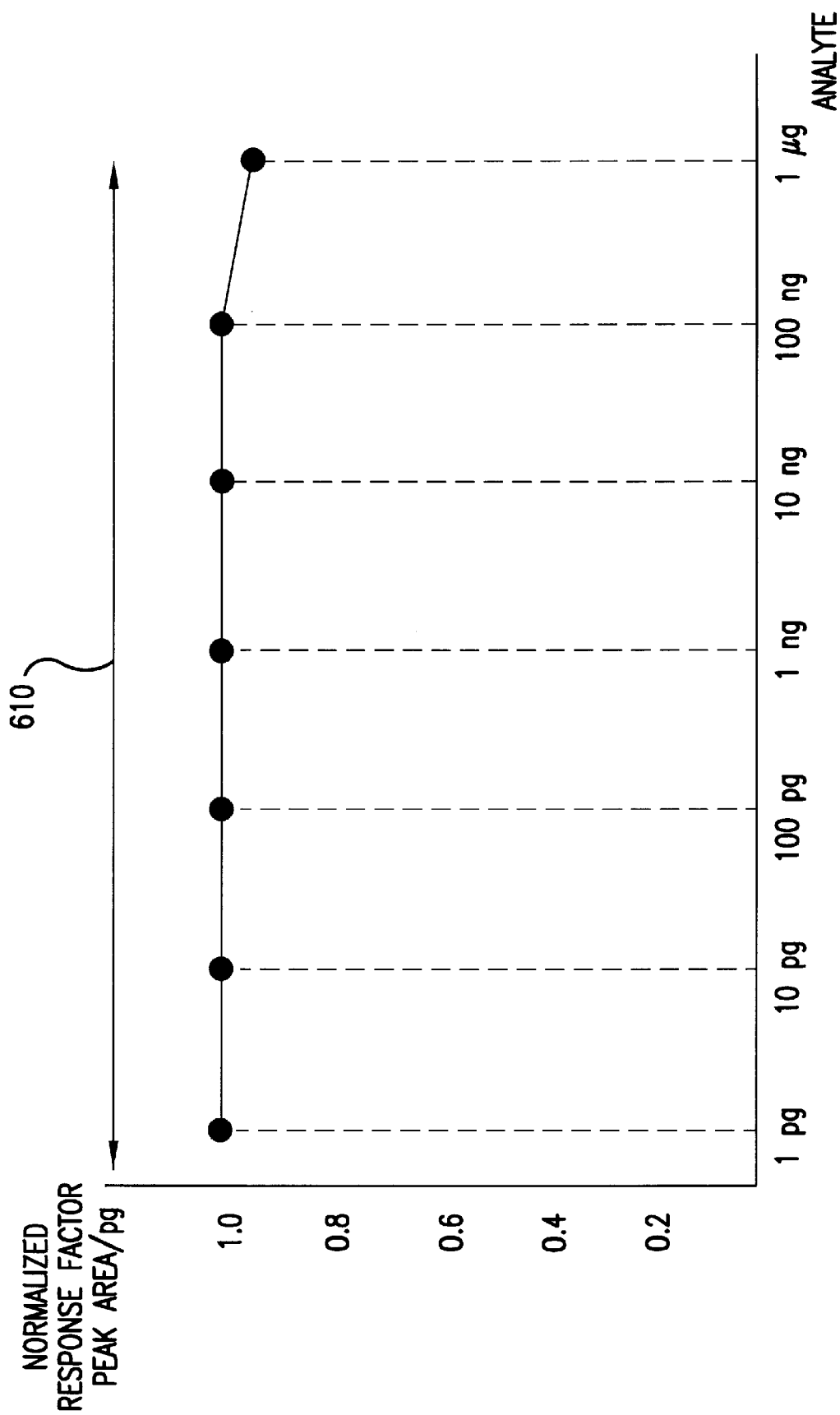
FIG. 5 is a graphical representation of an improved normalized response factor exhibited by an ionization detector constructed according to the present invention.

FIG. 5 illustrates the normalized response of a discharge ionization detector constructed according to the present invention. The detector response to a sample of carbon-12 is flat in a extended response region 410 and does not exhibit a reduction for amounts of analyte up to and including approximately one microgram.

What is claimed is:

1. A linearized ionization detector for detection of an analyte, comprising:

a non-linearized ionization detector having a detector output signal provided on an output signal line;

a linearizing section, connected to the output signal line, for linearizing the detector output signal and for providing a linearized output signal according to the linearizing formula:

$$I_{(lin)} = I[1 + (I/I_{(dec)})]^{pwr}$$

Where:

$I_{(lin)}$=linearized output signal current of the detector $I$=non-linearized output signal current of the detector $I_{(dec)}$=output signal current at which a logarithmic decay begins to decline pwr=a power factor that compensates for the slope of the logarithmic decay.

* * * * *